United States Patent
Kawai et al.

(10) Patent No.: US 7,833,321 B2
(45) Date of Patent: Nov. 16, 2010

(54) PROTECTIVE FILTER FOR EXTRACORPOREAL CIRCULATION CIRCUIT PRESSURE MONITOR

(75) Inventors: Katsunori Kawai, Osaka (JP); Akinobu Yamaguchi, Osaka (JP)

(73) Assignee: Nipro Corporation, Osaka (JP)

( * ) Notice: Subject to any disclaimer, the term of this patent is extended or adjusted under 35 U.S.C. 154(b) by 501 days.

(21) Appl. No.: 11/896,403

(22) Filed: Aug. 31, 2007

(65) Prior Publication Data

US 2008/0053906 A1    Mar. 6, 2008

(30) Foreign Application Priority Data

Sep. 4, 2006    (JP)    .............................. 2006-238796

(51) Int. Cl.
*B01D 53/22*    (2006.01)

(52) U.S. Cl. ........................... 96/6; 96/4; 96/11; 95/45; 95/46; 55/487; 55/501; 55/503; 55/510; 55/511; 73/706; 604/5.01; 210/640

(58) Field of Classification Search ........................ 96/4, 96/6, 11; 95/45, 46; 55/487, 495, 501, 503, 55/510, 511; 73/706; 604/5.01; 210/640
See application file for complete search history.

(56) References Cited

U.S. PATENT DOCUMENTS

| | | | | |
|---|---|---|---|---|
| 2,400,719 A | * | 5/1946 | Stackhouse | ................... 55/503 |
| 3,782,083 A | * | 1/1974 | Rosenberg | ................... 55/501 |
| 3,882,026 A | | 5/1975 | McPhee | ...................... 210/446 |
| 4,077,882 A | * | 3/1978 | Gangemi | ...................... 73/706 |
| 4,459,139 A | * | 7/1984 | vonReis et al. | ..................... 96/6 |
| 4,529,419 A | * | 7/1985 | Perl et al. | ......................... 96/6 |
| 4,874,513 A | * | 10/1989 | Chakraborty et al. | ......... 55/503 |
| 5,230,727 A | * | 7/1993 | Pound et al. | ................... 55/501 |
| 5,500,003 A | * | 3/1996 | Guala et al. | .................. 604/252 |
| 6,168,653 B1 | * | 1/2001 | Myers | ............................... 96/4 |
| 7,069,788 B2 | * | 7/2006 | Teugels | ........................ 73/706 |
| 7,175,697 B2 | * | 2/2007 | Neri | .............................. 55/511 |
| 7,520,919 B2 | * | 4/2009 | Caleffi | .............................. 96/4 |
| 2004/0237785 A1 | | 12/2004 | Neri | ............................... 96/7 |

FOREIGN PATENT DOCUMENTS

| | | | |
|---|---|---|---|
| GB | 2 043 478 A | * | 10/1980 |
| JP | 2001-129079 A | | 5/2001 |
| JP | 2004-337287 | * | 12/2004 |
| JP | 2004-337287 A | | 12/2004 |

* cited by examiner

*Primary Examiner*—Jason M Greene
(74) *Attorney, Agent, or Firm*—Kubovcik & Kubovcik

(57) ABSTRACT

There is provided a protective filter 1 for an extracorporeal circulation circuit pressure monitor, having a dialysis device side housing 2, an extracorporeal circulation circuit side housing 3, and a hydrophobic filter 4 held between both the housings, which allows passage of a gas but does not allow passage of a liquid, characterized in that a plurality of ribs 27 and 38 capable of supporting the hydrophobic filter 4 are respectively provided in both housings, and a protective member 5 for preventing direct contact between the ribs 38 and the hydrophobic filter 4 is interposed between the ribs 38 provided in the extracorporeal circulation circuit side housing 3 and the hydrophobic filter 4.

6 Claims, 4 Drawing Sheets

PROTECTIVE FILTER FOR EXTRACORPOREAL CIRCULATION CIRCUIT PRESSURE MONITOR

BACKGROUND OF THE INVENTION

The present invention relates to a protective filter for an extracorporeal circulation circuit pressure monitor. More specifically, the present invention relates to a protective filter for an extracorporeal circulation circuit pressure monitor which can reduce a load on a hydrophobic filter caused by pulsation of blood in a hemocatharsis therapy.

In an established hemocatharsis therapy such as hemodialysis, when blood is circulated to the extracorporeal circulation circuit by using a blood pump, the pressure of the blood in the extracorporeal circulation circuit is measured and a pressure fluctuation thereof is sensed. The pressure of blood in the extracorporeal circulation circuit is found by measuring a pressure transmitted to air contacting the blood in a drip chamber or the like with a pressure gage which is provided in the dialysis device through a pressure monitor line.

Usually, only air is filled in the pressure monitor line. However, in a case where an excessive pressure occurs in an inside of the extracorporeal circulation circuit by an increase in circulating blood flow rate, blood coagulation in the extracorporeal circulation circuit or an artificial kidney, or the like, blood enters into this pressure monitor line. If the blood reaches the pressure gage in the dialysis device, there is a problem that it becomes impossible to accurately measure the pressure in the extracorporeal circulation circuit. Further, if the blood or a blood-derived substance which has entered into an inside of the pressure gage reversibly flows to the extracorporeal circulation circuit, there is also a problem that it causes an infection.

Therefore, a conventional extracorporeal circulation circuit pressure monitor has a constitution in which there is provided a protective filter constituted by a dialysis device side housing, an extracorporeal circulation circuit side housing and a hydrophobic filter held between the housings (for example, Japanese Patent Laid-Open No. 2001-129079). The protective filter prevents blood or the like from entering into the inside of the pressure gage. In a conventional protective filter, a protective plate is vertically provided in a housing in order to support the hydrophobic filter in the housing. This protective plate is formed in order to suppress bulging of the hydrophobic filter and to prevent breaking of the filter. However, if the hydrophobic filter is caused to vibrate by pulsation of blood flowing in the extracorporeal circulation circuit, there is a problem that a portion of the filter which contacts the protective plate is broken by friction and that the blood leaks therefrom.

There is also developed a protective filter which is designed to prevent breakage of the filter (for example, Japanese Patent Laid-Open No. 2004-337287). The protective filter is comprised of an air pressure buffer member formed in the housing. The pressure on the filter is dispersed thereby and a load is prevented from being directly applied to the filter by the fluctuation of the pressure in the extracorporeal circulation circuit side. However, there is a problem also in this protective filter that the filter contacts the air pressure buffer member and is broken by the vibration of the filter due to the pulsation of the blood, so that an issue of blood leakage still exists.

SUMMARY OF THE INVENTION

In order to solve the above issues, an object of the present invention is to provide a protective filter for an extracorporeal circulation circuit pressure monitor, in which stable performance of a filter film can be brought about without the hydrophobic filter being broken even if pulsation of the blood occurs in the extracorporeal circulation circuit.

As a result of earnestly performing studies, it was found that the above problem could be solved by interposing a protective member between the hydrophobic filter and a plurality of ribs provided in the housing in order to prevent contact between the hydrophobic filter and the ribs which was a main cause of breakage of the hydrophobic filter.

That is, the present invention relates to a protective filter for an extracorporeal circulation circuit pressure monitor comprising of a dialysis device side housing having a lumen penetrating therethrough, an extracorporeal circulation circuit side housing having a lumen penetrating therethrough, and a hydrophobic filter held between the housings which allows passing of a gas but does not allow passing of a liquid, characterized in that a plurality of ribs for supporting the hydrophobic filter are respectively provided in both the housings, and a protective member capable of preventing direct contact between the ribs and the hydrophobic filter is interposed between the ribs provided in the extracorporeal circulation circuit side housing and the hydrophobic filter.

The protective filter for the extracorporeal circulation circuit pressure monitor of the present invention is also characterized in that the protective member is a disc or a disc having an opening at the center thereof.

The protective filter for the extracorporeal circulation circuit pressure monitor of the present invention is also characterized in that the ribs provided in the extracorporeal circulation circuit side housing are protruded toward an axis of the extracorporeal circulation circuit side housing from an inside wall of the extracorporeal circulation circuit side housing and arranged radially from the axis of the extracorporeal circulation circuit side housing, and the protective member is one capable of protecting against at least an axis side end part in a hydrophobic filter side end face of the ribs.

The protective filter for the extracorporeal circulation circuit pressure monitor of the present invention is also characterized in that the protective member is held between the housings together with the hydrophobic filter.

In the protective filter for the extracorporeal circulation circuit pressure monitor of the present invention, the hydrophobic filter does not directly contact the ribs since the protective member is provided between the hydrophobic filter and the ribs of the extracorporeal circulation circuit side housing. Even if pulsation of the blood occurs in the extracorporeal circulation circuit and thus the hydrophobic filter is caused to vibrate by pressure changes, there is no problem that the hydrophobic filter breaks. Therefore, the protective filter for the extracorporeal circulation circuit pressure monitor of the present invention is capable of bring about a stable performance of the filter film.

DESCRIPTION OF THE DRAWINGS

The protective filter for the extracorporeal circulation circuit pressure monitor of the present invention is described in detail below by referring to preferable embodiments shown in the appended drawings. However, the present invention is not limited to these embodiments.

DETAILED DESCRIPTION OF THE INVENTION

Figure 1:
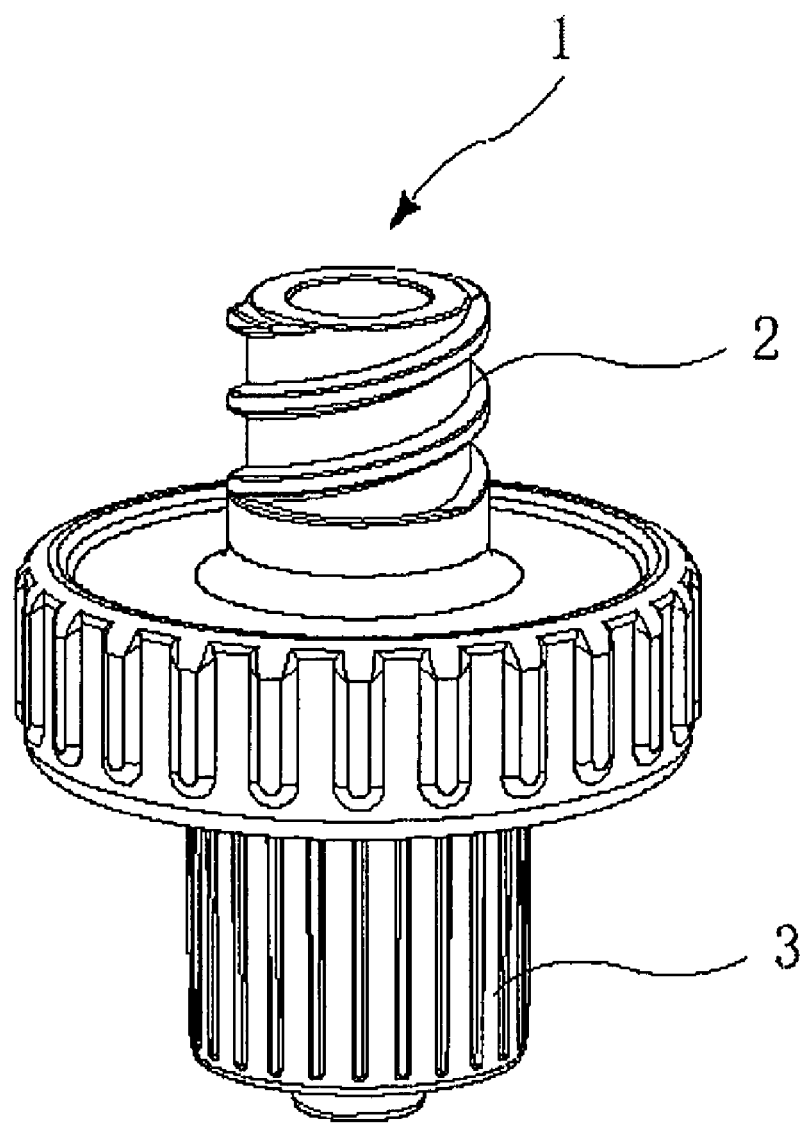
FIG. 1 is a perspective view of a protective filter for an extracorporeal circulation circuit pressure monitor of the present invention.
Figure 5A:
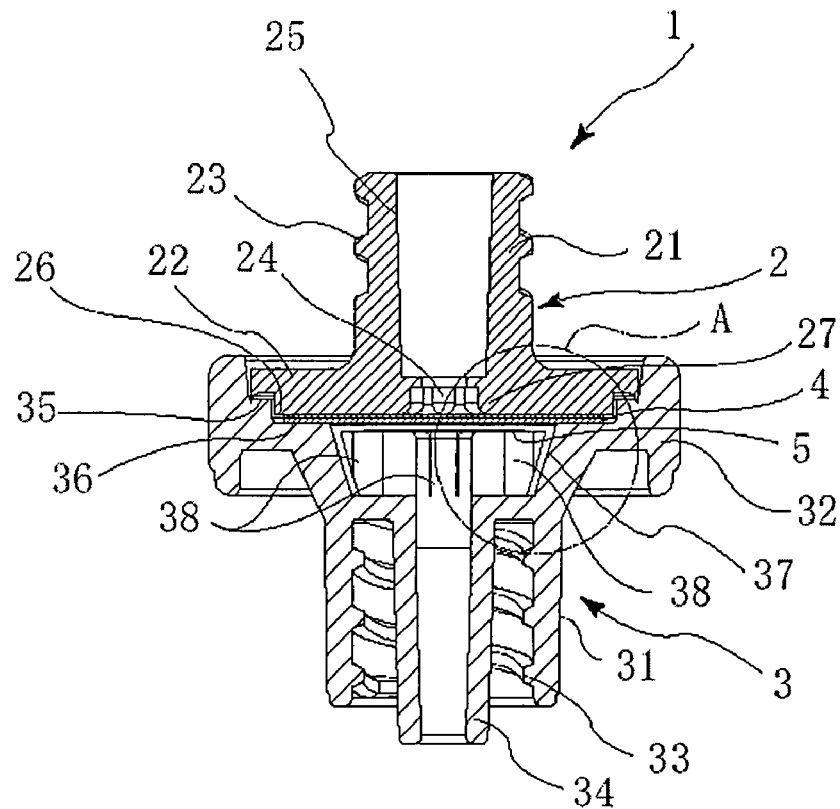
FIGS. 5(a) and 5(b) are sectional views showing embodiment of the protective filter for the extracorporeal circulation circuit pressure monitor, with which the present invention is concerned, wherein (a) is a whole sectional view and (b) is a partial enlarged sectional view.

The structure of the protective filter for an extracorporeal circulation circuit pressure monitor of the present invention is explained by using the perspective view shown in FIG. 1. As shown in the drawing, a protective filter 1 for the extracorporeal circulation circuit pressure monitor of the present invention is comprised of a dialysis device side housing 2 dimensioned and configured to be connected to a tube linked to a pressure gage in a dialysis device, and an extracorporeal circulation circuit side housing 3 dimensioned and configured to be connected to a tube linked to an extracorporeal circulation circuit. There is held a hydrophobic filter 4 between both the housings as shown in FIGS. 5 and 6. Additionally, a protective member 5 is interposed between the extracorporeal circulation circuit side housing 3 and the hydrophobic filter 4.

Figure 2:
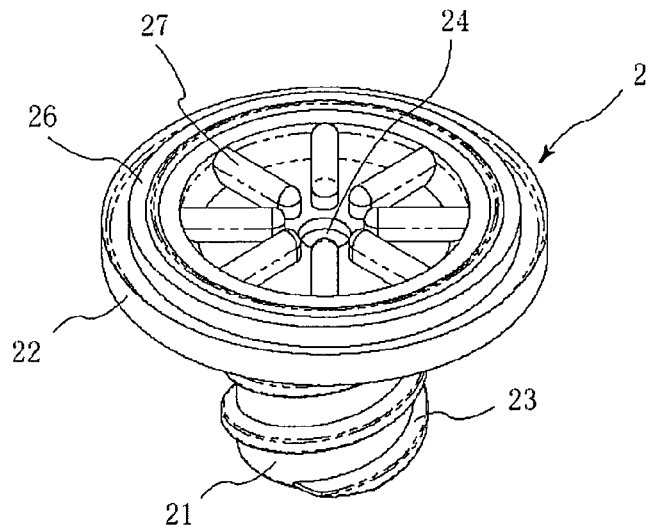
FIG. 2 is a perspective view showing one embodiment of a dialysis device side housing of the protective filter for the extracorporeal circulation circuit pressure monitor shown in FIG. 1.

As shown in FIGS. 2 and 5, the dialysis device side housing 2 is formed by a connection part 21 dimensioned and configured to be connected to a tube linked to the pressure gage in the dialysis device and a filter support part 22 supporting the hydrophobic filter 4. Both the connection part 21 and the filter support part 22 have a structure such that there is formed in the dialysis device side housing 2 a penetrating lumen 24 which centers on an axis of the housing 2. The connection part 21 may include a thread part 23 and a taper part 25 for connecting to a connector provided at an end of the tube linked to the pressure gage by using a lock mechanism. The dialysis device side housing 2 is molded of a hard resin of a thermoplastic such as polycarbonate, polypropylene, ABS, and polyvinyl chloride.

The filter support part 22 of the dialysis device side housing 2 has a size capable of supporting the entire surface of the hydrophobic filter 4. The filter support part 22 includes a convex part 26 at the hydrophobic filter side thereof for fixing by welding to an edge part of the hydrophobic filter 4. The filter support part 22 is fitted to a later-mentioned filter support part 32 of the extracorporeal circulation circuit side housing 3 at an outer periphery face of the filter support part 22, and firmly connected by welding a contact area between the filter support parts 22 and 32.

In the filter support part 22, a plurality of ribs 27 are provided to protrude toward an axis of the dialysis device side housing 2 from an inside wall of the housing 2 in order to suppress the vibration of the hydrophobic filter 4 caused by pulsation of the blood. Each of ribs 27 is a plate-like member and is arranged radially from the axis of the dialysis device side housing 2. Although the number of ribs 27 is not especially limited, from three to ten ribs are preferably provided, and in the implementation mode shown in the drawings, eight are provided.

Figure 3:
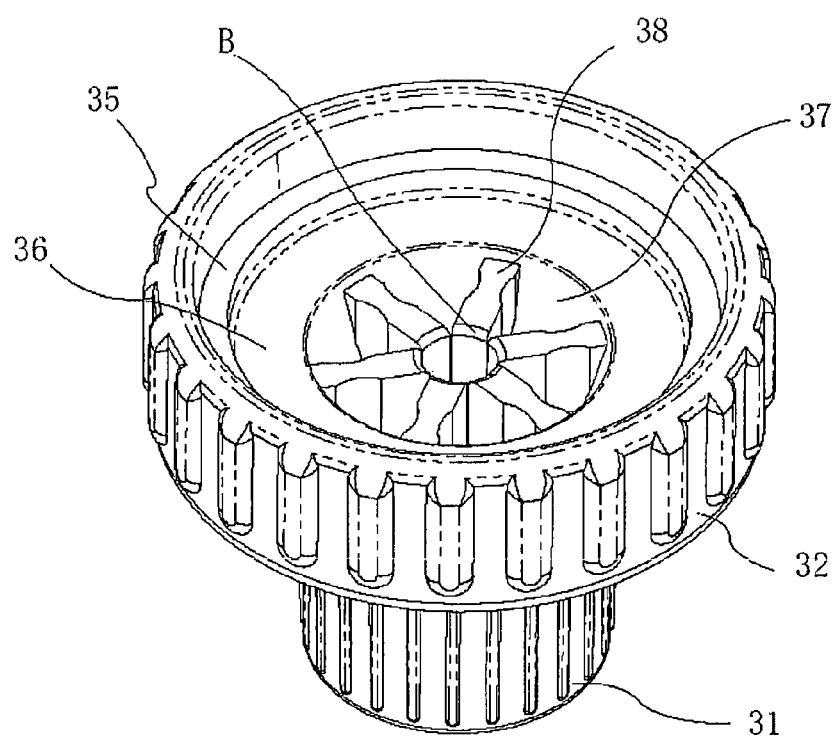
FIG. 3 is a perspective view showing one embodiment of an extracorporeal circulation circuit side housing of the protective filter for the extracorporeal circulation circuit pressure monitor shown in FIG. 1.

As shown in FIGS. 3 and 5, the extracorporeal circulation circuit side housing 3 is formed by a connection part 31 dimensioned and configured to be connected to a tube linked to the extracorporeal circulation circuit and a filter support part 32 capable of supporting the hydrophobic filter 4. Both the connection part 31 and the filter support part 32 have a structure such that there is formed in the extracorporeal circulation circuit side housing 3 a penetrating lumen which centers on the axis of the housing 3. Similarly to the connection part 21 of the dialysis device side housing 2, the connection part 31 may include a thread part 33 and a taper part 34 for connecting to a luer lock type connector provided at an end of a tube linked to the extracorporeal circulation circuit. The extracorporeal circulation circuit side housing 3 is also molded of a hard resin of a thermoplastic such as polycarbonate, polypropylene, ABS, and polyvinyl chloride.

In the filter support part 32 of the extracorporeal circulation circuit side housing 3, there is formed a first cylindrical concave part 35 which has a size capable of accommodating the filter support part 22 of the dialysis device side housing 2 and is centered on the axis of the extracorporeal circulation circuit side housing 3, and a second cylindrical concave part 36 which has a size to which the hydrophobic filter 4 is welded and is centered on the axis of the housing 3 inside the first cylindrical concave part 35. The first cylindrical concave part 35 is fitted to the outer periphery face of the filter support part 22 of the dialysis device side housing 2 at an edge of the first cylindrical concave part. The dialysis device side housing 2 and the extracorporeal circulation circuit side housing 3 are firmly connected in a state holding the hydrophobic filter 4 by welding the contact area between the first cylindrical concave part 35 and the outer periphery face of the filter support part 22. In this state, the lumen 24 of the dialysis device side housing 2 and the lumen of the extracorporeal circulation circuit side housing 3 communicate through the hydrophobic filter 4, and gas permeation between the lumens is hindered.

Additionally, there is formed a third cylindrical concave part 37 which is centered on the axis of the extracorporeal circulation circuit side housing 3 inside the second cylindrical concave part 36. In the third cylindrical concave part 37, a plurality of ribs 38 are provided to protrude toward the axis of the extracorporeal circulation circuit side housing 3 from the inside wall of the extracorporeal circulation circuit side housing 3 in order to suppress vibration of the hydrophobic filter 4 caused by pulsation of the blood. Each of ribs 38 is a plate-like member and is arranged radially from the axis of the extracorporeal circulation circuit side housing 3. Although the number of ribs 38 is not especially limited, from three to ten ribs are preferably provided, and in the implementation mode shown in the drawings, six are provided.

The hydrophobic filter 4 is a hydrophobic filter which allows a gas to permeate therethrough but does not allow a liquid such as blood and a physiological salt solution to pass therethrough, and has desirably a disc shape. As a material of the hydrophobic filter 4, one not allowing the passing of microorganisms, suspended dust or the like is desirable, and it is possible to adopt, e.g., polytetrafluoroethylene or the like. The hydrophobic filter 4 may be overlapped with a support film 41 formed of polyethylene terephthalate or the like at one side of the hydrophobic filter 4 for increasing the strength thereof. It is desirable that the hydrophobic filter 4 does not cause pressure loss of the gas which permeates from the extracorporeal circulation circuit side housing 3 to the dialysis device side housing 2. Although an outer diameter of the hydrophobic filter 4 is not especially limited, when the outer diameter of the hydrophobic filter 4 is same as an outer diameter of the convex part 26 or an inner diameter of the second cylindrical concave part 36, the arrangement of the hydrophobic filter 4 is useful.

The protective member 5 interposed between the extracorporeal circulation circuit side housing 3 and the hydrophobic filter 4 is a disc or a disc having an opening at the center thereof. It is necessary that the protective member 5 does not cause pressure loss of the gas which permeates from the extracorporeal circulation circuit side housing 3 to the dialysis device side housing 2. Accordingly, as the protective member 5, there is desirably used a porous body of polyethylene, polypropylene, fluororesin, polyurethane, polystyrene or the like, or a nonwoven fabric etc. of polyethylene terephthalate or the like. Further, it is desirable that the size of the pores of the protective member 5 be 1-100 μm, and that the film thickness be 0.1-1 mm.

Figure 5B:
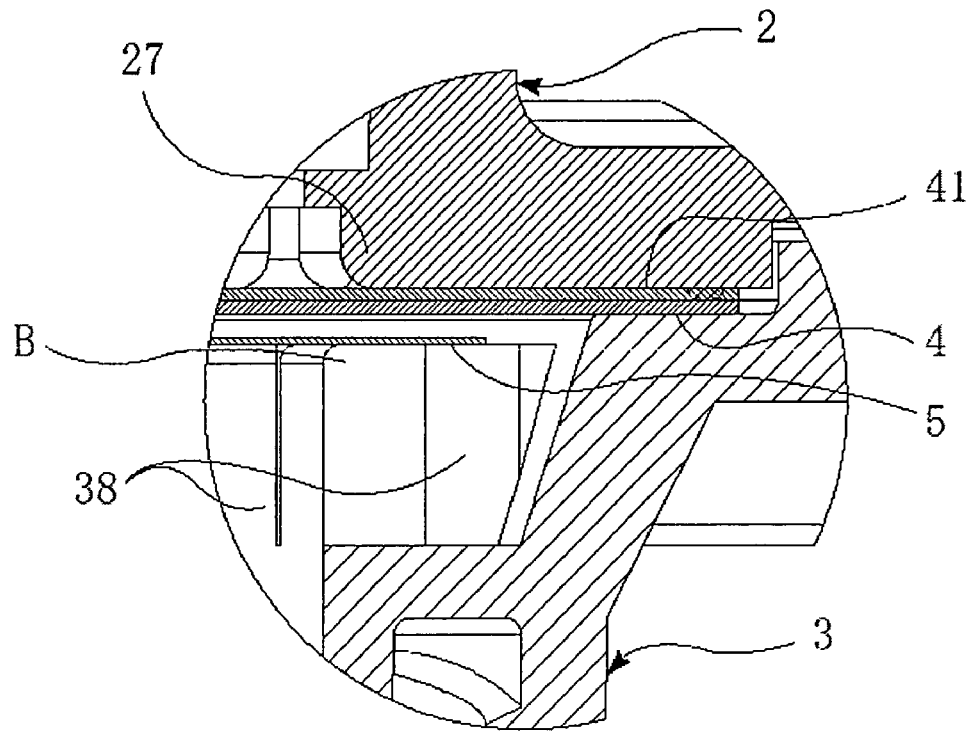
Figure 6A:
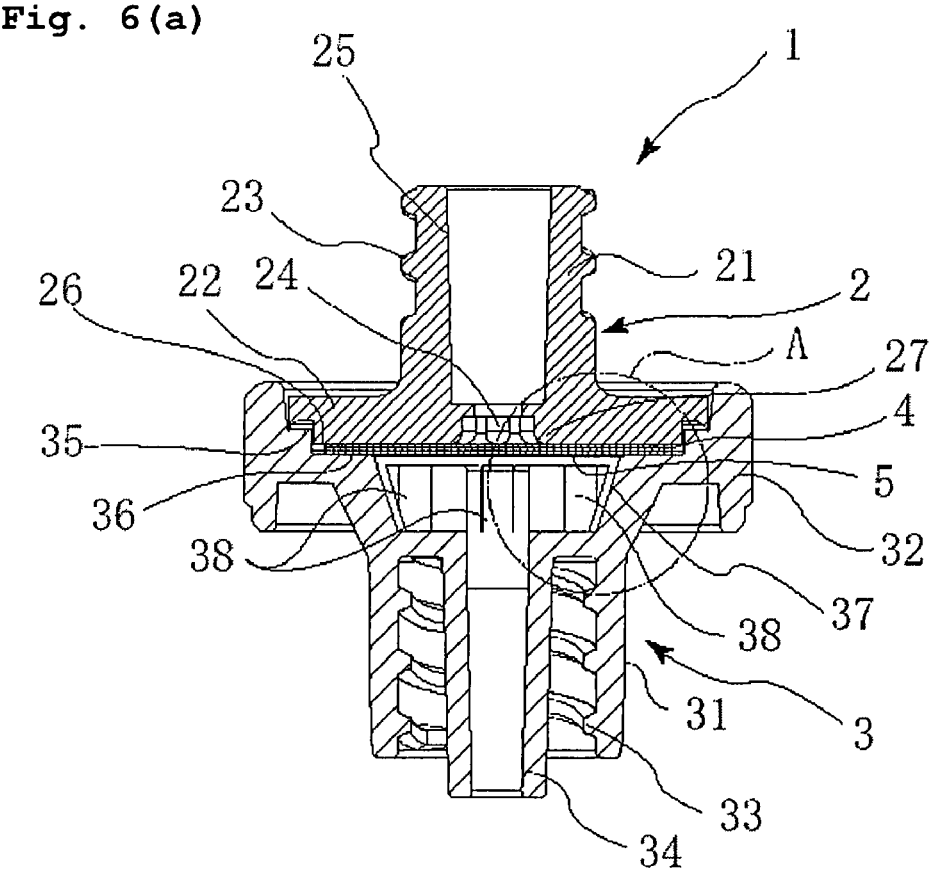
FIGS. 6(a) and 6(b) are sectional views showing other embodiment of the protective filter for the extracorporeal circulation circuit pressure monitor, with which the present invention is concerned, wherein (a) is a whole sectional view and (b) is a partial enlarged sectional view.
Figure 6B:
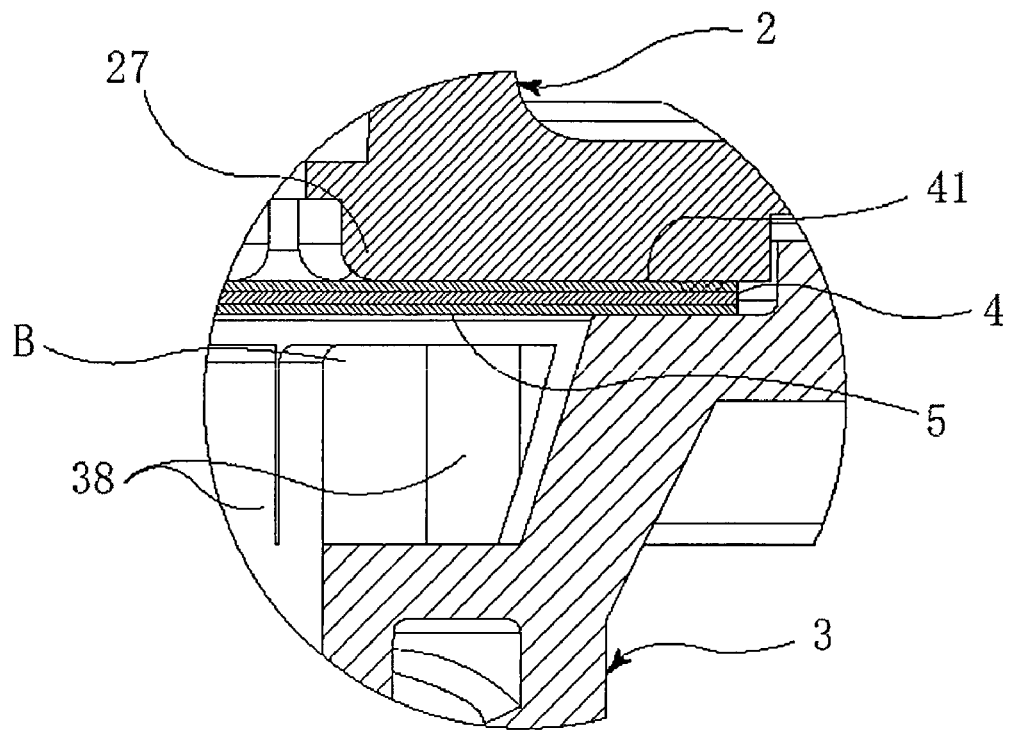

As can be understood from FIG. 5(b), breakage of the hydrophobic filter 4 by the vibration resulting from pulsation of the blood in the extracorporeal circulation circuit has occurred mainly because the hydrophobic filter 4 contacts a axis side end part B in a hydrophobic filter 4 side end face of the ribs 38 provided in the extracorporeal circulation circuit side housing 3. The protective member 5 is provided in order to prevent direct contact between the hydrophobic filter 4 and the axis side end part B. As shown in FIG. 5(b) for instance, the protective member 5 has a shape in which it is interposed on the hydrophobic filter 4 side end face of the ribs 38 in the third cylindrical concave part 37 of the extracorporeal circulation circuit side housing 3. When the dialysis device side housing 2 to which the hydrophobic filter 4 is welded and the extracorporeal circulation circuit side housing 3 are fitted together, the protective member 5 is mounted on the hydrophobic filter 4 side end face of the ribs 38 and interposed between the housings. Since the hydrophobic filter 4 is prevented from directly contacting with ribs 38 provided in the extracorporeal circulation circuit side housing 3 by such protective member 5, there is no problem that the hydrophobic filter 4 is broken by pulsation of blood in the extracorporeal circulation circuit.

Figure 4A:
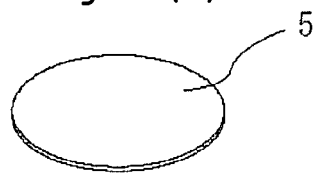
FIGS. 4(a) and 4(b) are perspective views showing embodiments of a protective member of the protective filter for the extracorporeal circulation circuit pressure monitor shown in FIG. 1.
Figure 4B:
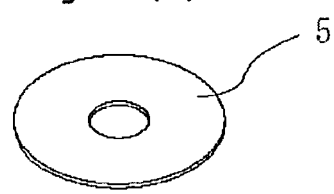

The protective member 5 may be a disc as shown in FIG. 4(a) or a disc having an opening at the center thereof as shown in FIG. 4(b) since the protective member 5 is capable of protecting at least the axis side end part B in the hydrophobic filter side end face of the ribs 38. Therefore, the opening at the center of the disc shown in FIG. 4(b) may have a diameter which is smaller than a diameter of a lumen settled by the axis side end part B in the extracorporeal circulation circuit side housing 3 and may be arranged in the position that a center of the opening corresponds to the lumen settled by the axis side end part B when the protective member 5 is interposed between the housings. When an outer diameter of the protective member 5 is same as an inner diameter of the third cylindrical concave part 37, the arrangement of the opening of the protective member 5 is useful.

Additionally, as shown in FIG. 6, the protective member 5 may have the same shape as the hydrophobic filter 4 and be held between the housings together with the hydrophobic filter 4. When the dialysis device side housing 2 to which the hydrophobic filter 4 is welded and the extracorporeal circulation circuit side housing 3 are fitted together, the protective member 5 is mounted in the first cylindrical concave part 35 of the extracorporeal circulation circuit side housing 3 and held between the housings together with the hydrophobic filter 4. Since the hydrophobic filter 4 is prevented from directly contacting the ribs 38 provided in the extracorporeal circulation circuit side housing 3 by such protective member 5, there is no problem that the hydrophobic filter 4 is broken by the pulsation of blood in the extracorporeal circulation circuit.

This application claims priority of Japanese Patent Application No. 2006-238796 filed Sep. 4, 2006, which is incorporated herein by reference.

What is claimed is:

1. A protective filter for an extracorporeal circulation circuit pressure monitor, having a dialysis device side housing having a lumen penetrating therethrough, an extracorporeal circulation circuit side housing having a lumen penetrating therethrough, and a hydrophobic filter held between the housings, said filter allowing passage of a gas but not allowing passage of a liquid, characterized in that a plurality of ribs capable of supporting the hydrophobic filter are respectively provided in both housings, and a protective member capable of preventing direct contact between the ribs provided in the extracorporeal circulation circuit side housing and the hydrophobic filter is interposed between the ribs provided in the extracorporeal circulation circuit side housing and the hydrophobic filter, the protective member being porous and having pores having a size of 1-100 μm; and the protective member having a thickness of 0.1-1 mm.

2. The protective filter for the extracorporeal circulation circuit pressure monitor according to claim 1, characterized in that the protective member is a disc or a disc having an opening at the center thereof.

3. The protective filter for the extracorporeal circulation circuit pressure monitor according to claim 1, characterized in that the ribs provided in the extracorporeal circulation circuit side housing are protruded toward an axis of the extracorporeal circulation circuit side housing from an inside wall of the extracorporeal circulation circuit side housing and arranged radially from the axis of the extracorporeal circulation circuit side housing, and the protective member is one capable of protecting against at least an axis side end part in a hydrophobic filter side end face of the ribs.

4. The protective filter for the extracorporeal circulation circuit pressure monitor according to claim 1, characterized in that the protective member is held between both housings together with the hydrophobic filter.

5. The protective filter for the extracorporeal circulation circuit pressure monitor according to claim 2, characterized in that the ribs provided in the extracorporeal circulation circuit side housing are protruded toward an axis of the extracorporeal circulation circuit side housing from an inside wall of the extracorporeal circulation circuit side housing and arranged radially from the axis of the extracorporeal circulation circuit side housing, and the protective member is one capable of protecting against at least an axis side end part in a hydrophobic filter side end face of the ribs.

6. The protective filter for the extracorporeal circulation circuit pressure monitor according to claim 2, characterized in that the protective member is held between both housings together with the hydrophobic filter.

* * * * *